United States Patent [19]

Toyomaki et al.

[11] Patent Number: 4,985,354

[45] Date of Patent: Jan. 15, 1991

[54] METHOD OF ASSAYING KALLIKREIN FORMATION SUBSTANCES

[75] Inventors: Yoshio Toyomaki; Katsumi Nishikawa; Hitoshi Kawakubo, all of Hyogo, Japan

[73] Assignee: Nippon Zoki Pharmaceutical Co., Ltd., Osaka, Japan

[21] Appl. No.: 95,821

[22] Filed: Sep. 10, 1987

[30] Foreign Application Priority Data

Sep. 10, 1986 [JP] Japan ................................ 61-214959

[51] Int. Cl.$^5$ .................... C12Q 1/37; C12Q 1/56; G12N 9/99
[52] U.S. Cl. ......................................... 435/13; 435/23; 435/24; 435/184; 436/69
[58] Field of Search ................. 436/69; 435/13, 23, 435/24, 184

[56] References Cited

PUBLICATIONS

Bergmeyer, H. U., vol. II, "Samples, Reagents, Assessment of Results", in *Methods of Enzymatic Analysis*, (Verlag Chemie, Weinheim, Germany), pp. 442 and 445.

Bergmeyer, H. U., vol. V, "Enzymes 3: Peptidases, Proteinases, and Their Inhibitors", in *Methods of Enzymatic Analysis*, (Verlag Chemie, Weinheim, Germany), pp. 338 and 411-418, (1984).

Hojima, Y. et al., *Biochemistry*, 21:3741-3746, (1982).

*Primary Examiner*—Esther L. Kepplinger
*Assistant Examiner*—Toni R. Scheiner
*Attorney, Agent, or Firm*—Oliff & Berridge

[57] ABSTRACT

A method of assaying a physiologically active substance, which comprises activating blood coagulation factor XII in plasma in the presence of said physiologically active substance being tested to convert prekallikrein in the plasma into kallikrein, and measuring the activity of kallikrein thus formed.

13 Claims, 1 Drawing Sheet

METHOD OF ASSAYING KALLIKREIN FORMATION SUBSTANCES

BACKGROUND OF THE INVENTION

1. Field of the Invention

This invention relates to a method of assaying physiologically active substances. More particularly, it relates to a method of assaying physiologically active substances involved in the process of plasma kallikrein formation.

2. Description of the Prior Art

Kallikrein is a group of protease widely distributed in the plasma and tissues of animals, and is known to participitate in an enzyme reaction system called kallikrein-kinin system.

This kallikrein-kinin system is closely related to many other enzyme reaction systems, such as the renin-angiotensin system, the blood coagulation system, the fibrinolysis system, the complement system, and the arachidonate cascade producing prostaglandin, leukotriene and thromboxane, as well as to the behavior of catecholamine, thus playing an important role for function control in living bodies. To be more specific, it is deeply concerned, through other enzyme reaction systems, with blood pressure control, control actions relating to blood coagulation fibrinolysis-complement system, and peripheral blood circulation improvement and other control actions exerted by various physiologically active substances produced from the arachidonate cascade.

It is known that plasma kinin, which is a product of the kallikrein-kinin system, shows various physiological actions, such as hypotensive action as a result of vasodilation, enhancement of vascular permeability, contraction and relaxation of smooth muscles, development of pains, leucocytes chemotaxis, and liberation of catecholamine from the adrenal cortex. It is also known that plasma kinin acts as a mediator for acute inflammations, including allergic reactions. Thus the presence of plasma kinin in living bodies is of great significance.

Hence, establishing a simple method for correctly evaluating the action of substances involved in the formation of kallikrein ( substances that retard or accelerate the formation of kallikrein ) would be of great use in learning the aforementioned actions for function control in living bodies and also in developing new drugs having such actions.

The kallikrein-kinin system involves a series of enzyme reactions as described below.

Blood coagulation factor XII ( Hageman factor; hereinafter abbreviated as F-XII ) is the substance which plays the major role in this enzyme reaction system. F-XII in the plasma is activated upon contact with a negatively charged substance ( such as glass, kaolin and elaidic acid ) or with a substance existing in living bodies ( such as collagen, homocystine, platelet membrane and sulfated glycolipid ), or as a result of nociceptive stimulation upon tissues. The resulting activated F-XII ( F-XIIa ) then acts upon prekallikrein present in the plasma to convert it into kallikrein, which in turn acts upon high-molecular-weight kininogen in the plasma, liberating bradykinin which is a nonapeptide.

Eventually, the kinin thus formed causes inflammations and pains, and exerts various influences on living bodies through action upon the arachidonate cascade.

In-vitro simulation of the aforementioned series of enzyme reactions related to the kallikrein-kinin system has led us to find that the reaction system adopted in this invention provides a simple, highly reliable, and most effective method for assaying physiologically active substances. This invention was accomplished based on these findings.

SUMMARY OF THE INVENTION

An object of this invention is to provide a method for assaying physiologically active substances involved in the formation of kallikrein.

Another object of this invention is to provide a method for determining whether a substance (a drug) is involved in the formation of kallikrein or not.

A further object of this invention is to provide a method for measuring the extent to which a physiologically active substance is involved in the formation of kallikrein.

A still further object of this invention is to provide a reaction system best suited to the method mentioned above.

DETAILED DESCRIPTION OF THE INVENTION

Figure 1:
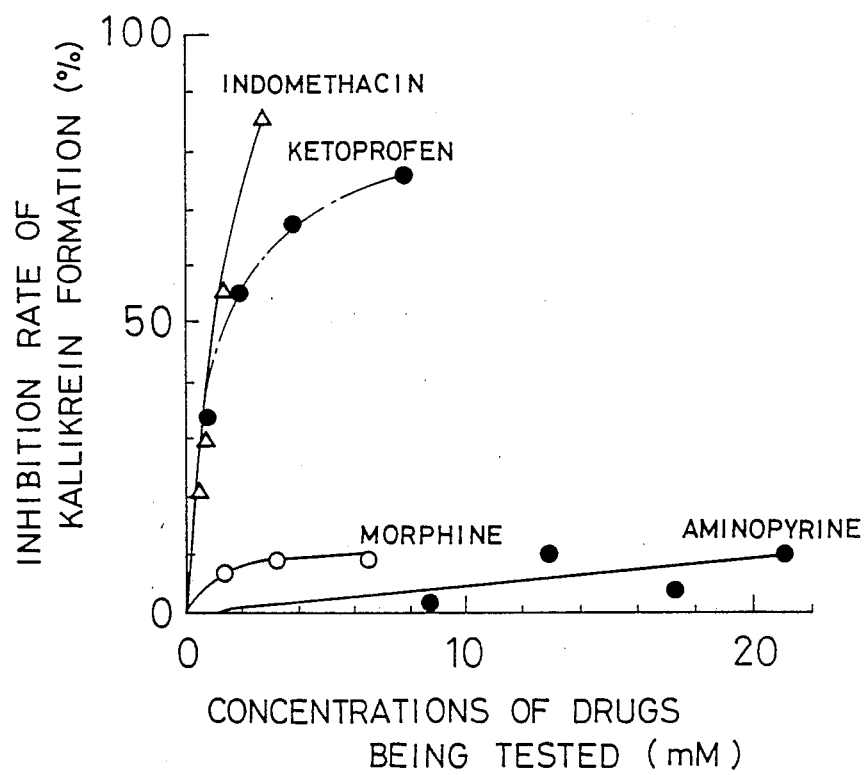
FIG. 1 is a graph showing the inhibitory actions of various analgesics against the formation of kallikrein measured by the method of this invention.

This invention relates to a method of assaying a physiologically active substance, which comprises activating F-XII in the plasma in the presence of said physiologically active substance (a drug being tested) to convert prekallikrein contained in the plasma into kallikrein by the action of F-XIIa thus formed, and measuring the amount of the resulting kallikrein.

More specifically, this invention relates to a method of assaying a physiologically active substance, which comprises allowing a reaction to proceed by mixing (1) animal plasma, (2) an activator for blood coagulation factor XII, (3) an electrolyte and (4) a drug being tested; adding an inhibitor having practically no action upon the kallikrein activity and capable of specifically inhibiting the activity of the activated blood coagulation factor XII; and measuring the amount of kallikrein thus formed.

In a preferred embodiment of this invention, a reaction is allowed to proceed by mixing (1) animal plasma, (2) an activator for blood coagulation factor XII, (3) an electrolyte and (4) a drug being tested, and an inhibitor having practically no action upon the kallikrein activity and capable of specifically inhibiting the activity of the activated blood coagulation factor XII is then added. To the resulting mixture is added a solution of a substrate for kallikrein in a buffer solution, and the amount of decomposition product formed by the action of kallikrein is measured, thereby determining the efficacy of drug being tested.

The reaction system adopted in the method of this invention involves two steps as described above. The primary reaction is a step in which F-XII in the plasma is converted into F-XIIa by addition of an activator, such as kaolin, which in turn acts upon prekallikrein to form kallikrein. The secondary reaction that follows is a step in which the amount of kallikrein formed is measured; for example, the activity (or quantity) of kallikrein may be determined by the use of a substrate specific to kallikrein.

Thus, the method of this invention is characterized in that a physiologically active substance involved in the formation of kallikrein is allowed to be present in the primary reaction system mentioned above, and its quantity is determined in the secondary reaction system.

In the method of this invention, plasma of any type of animal may be used so long as it contains the blood coagulation and kallikrein-kinin systems. This includes plasma of humans, monkeys, cattle, sheeps, pigs, horses, goats, dogs, cats, rabbits, guinea pigs, rats and mice. Of these, the plasma of humans and rats are the most preferred.

Plasma used in the method of this invention may be prepared by any known methods. For example, a blood sample taken in the presence of sodium citrate is centrifuged and the resulting supernatant may be used as citrate-containing plasma. Freeze-dried plasma prepared by usual method may also be used for the purpose of this invention.

The animal plasma thus prepared may be appropriately diluted, as required, before use. Its concentration should be within the range over which a linear relationship holds between its dilution and the kallikrein activity.

A variety of substances may be used as the activator for F-XII in the method of this invention. These include kaolin, collagen, dextran sulfate, elaidic acid and Celite. To ensure satisfactory activation of F-XII, each of these activators should be used at its optimum concentration. For example, when an aqueous suspension of kaolin is used for human plasma, its final concentration should preferably be in the range of 1 to 3 mg/ml, most preferably, in the range of 1.25 to 2 mg/ml.

The electrolyte is added to make the action of the F-XII activator perfect. Preferable examples are those containing monovalent cation (e.g., sodium), such as sodium chloride, and sodium acetate.

With human plasma, for example, the final concentration of sodium chloride in the primary reaction should preferably be in the range of 50 to 200 mM, most preferably, in the range of 75 to 150 mM.

If the primary reaction is allowed to proceed at an elevated temperature, it progresses too rapidly and at the same time endogenous inhibitors are put to work, thus significantly affecting the measurement of kallikrein activity. It is therefore preferable to carry out the primary reaction at a low temperature (for example, at 0° to 4° C.) so that it will proceed slowly and endogenous inhibitors will not work.

The primary reaction should preferably be carried out at the optimum pH for kallikrein which is the final product of this reaction step; when human or rat plasma is used, the suitable pH is in the range of 7.0 to 9.0, most preferably, in the range of 7.5 to 8.5.

The suitable reaction time may vary with the amounts of plasma and F-XII activator added, the concentration of the drug being tested and the pH of the reaction system, but it should be set within the range over which a linear relationship holds between the reaction time and the amount of kallikrein formed (or kallikrein activity). This is because the method of this invention assays the activity involved in the formation of plasma kallikrein of a physiologically active substance as kallikrein activity and hence activity measurement must be made at a moment before the amount of kallikrein becomes saturated and when the aforementioned linear relationship still holds. In actual practice, however, it is preferable to set the reaction time within the range of 15 to 30 minutes.

The primary reaction may be terminated by addition of an inhibitor which specifically inhibits the activity of activated F-XII to prevent formation of extra kallikrein and shows practically no effect upon the activity of kallikrein to be measured in the secondary reaction.

As examples of such inhibitors, there may be mentioned LBTI (Lima Bean Trypsin Inhibitor) and CHFI (Corn Hageman Fragment Inhibitor). These inhibitors should be added at the end of the primary reaction in such an amount as to completely inhibit the activity of F-XIIa left in the primary reaction mixture and as to show practically no effect upon measurement of Kallikrein in the secondary reaction. When human plasma is used, for example, LBTI should preferably be added at a final concentration of 4 to 15 mg/ml.

As described above, the secondary reaction is a step for measuring the amount of kallikrein formed in the primary reaction, preferably by the use of a substrate specific to kallikrein.

A variety of substances may be used as the substrate specific to kallikrein. These include high-molecular-weight kininogen present in the plasma, and synthetic substrates such as N-benzoyl-N-arginine ethyl ester (Benzoyl-Arg-OEt), N-tosyl-L-arginine methyl ester (Tos-Arg-OMe), D-prolylphenylalanylarginyl-p-nitroanilide (D-Pro-Phe-Arg-pNA), benzoylprolyl-phenylalanylarginyl-p-nitroanilide (Benzoyl-Pro-Phe-Arg-pNA), prolylphenylalanylargininylnaphthylamide ( Pro-Phe-Arg-NA) and benzyloxycarbonyl-phenylalanylarginyl-4-methylcoumarinamide (Z-Phe-Arg-MCA).

When high-molecular-weight kininogen is used as the substrate, bradykinin thus formed can be determined by commonly employed techniques—through bioassay using smooth muscles like the guinea-pig ileum or rat myometrium (Magnus method), or through radioimmunoassay (RIA).

When the activity of kallikrein is measured by utilizing its esterase action, Benzoyl-Arg-OEt or Tos-Arg-OMe may be used as the substrate. The quantity of kallikrein may be determined by various methods. These include measuring the change in absorbance due to hydrolysis; spectrophotometric determination after conversion into a colored derivative [e.g., the hydroxamate method and the method using chromotropic acid or MBTH (3-methyl-3-benzothiazolonehydrazine)]; fluorometric determination after conversion into a fluorescent derivative; the method using alcohol dehydrogenase; and radiochemical determination by the use of a radioactive synthetic substrate.

In addition, D-Pro-Phe-Arg-pNA, Benzoyl-Pro-Phe-pNA and Z-Phe-Arg-MCA may also be used as a colored or fluorescent synthetic peptide substrate. In this case, the activity of kallikrein can be determined by spectrophotometric measurement of the colored or fluorescent substance formed by its hydrolytic action, for example, pNA (p-nitroaniline) and AMC (7-amino-4-methylcoumarin).

In the secondary reaction, the pH should preferably be maintained in the range of 7.0 to 9.0 (in the vicinity of the optimum pH for kallikrein), and the reaction temperature maintained in the range of 20° to 40° C. (in the vicinity of the optimum temperature for kallikrein; room temperature). The suitable reaction time may vary with the temperature, pH and substrate concentration, but it should be set within about 30 minutes to ensure high operation efficiency.

EXAMPLE 1

An example in which human plasma was used as animal plasma is detailed below.

(1) Preparation of Citrate-Containing Human Plasma

A blood sample, taken from a healthy adult in the presence of sodium citrate according to the commonly used procedure (human blood: 3.8% sodium citrate=9:1), was centrifuged, and the supernatant was collected as citrate-containing human plasma (hereinafter referred to simply as human plasma).

(2) Primary Reaction

| Human plasma | 0.1 ml |
|---|---|
| Aqueous suspension of kaolin | 0.5 ml |
| Aqueous solution of sodium chloride<br>Aqueous solution of drug being tested<br>Distilled water | 0.4 ml |

In the above formulation, the human plasma had been diluted with physiological saline to such a concentration that kallikrein activity of 1.6 to 2.2 mU will be shown in the secondary reaction. For kallikrein activity, its amount that produces 1 μmole/min/ml of p-nitroaniline in the secondary reaction was taken as 1 U (1,000 mU).

The concentration of kaolin suspension was 2.5 mg/ml [in 50 mM Tris-HCl buffer (pH 8.0)], and that of sodium chloride in the mixed solution (0.4 ml) was 0.25M.

The above mixture was allowed to stand in an ice-/water bath for 20 minutes to effect the primary reaction, which was terminated by addition of 0.5 ml LBTI solution [45 mg/ml in 50 mM Tris-HCl buffer (pH 8.0)] to make the primary reaction mixture. It may also be prepared by taking 0.2 ml of the reaction mixture before termination and adding it to 0.1 ml of LBTI solution.

(3) Secondary Reaction

| Primary reaction mixture | 0.1 ml |
|---|---|
| Synthetic substrate | 0.1 ml |
| Buffer solution | 0.2 ml |

In the above formulation, the synthetic substrate was 4 mM aqueous solution of D-Pro-Phe-Arg-pNA, and the buffer solution was 100 mM Tris-HCl buffer (pH 8.0).

The above mixture was allowed to stand at 30° C. for 20 minutes to effect the secondary reaction, 0.8 ml of 1% citric acid was added, suspended solids, if any, were removed by centrifugation, and the amount of p-nitroaniline was determined by measuring the absorbance at 405 nm.

(4) Optimum pH for the Primary Reaction

The primary reaction was carried out using 50 mM Tris-HCl buffer solutions of different pH levels. The activity of kallikrein thus formed was measured in the succeeding secondary reaction, which showed that the optimum pH for the primary reaction lies within the range of 7.0 to 9.0, particularly, within the range of 7.5 to 8.5.

(5) Optimum Sodium Chloride Concentration in the Primary Reaction

The primary reaction was carried out using sodium chloride solutions of different concentrations. The activity of kallikrein thus formed was measured in the succeeding secondary reaction, which showed that the optimum final concentration of sodium chloride in the primary reaction lies within the range of 50 to 200 mM, particularly, within the range of 75 to 150 mM.

Note that the amount of sodium chloride contained in plasma is not included in the above concentrations.

(6) Optimum Kaolin Concentration in the Primary Reaction

The primary reaction was carried out in 50 mM Tris-HCl buffer solution (pH 8.0) using kaolin suspension of different concentrations. The activity of kallikrein thus formed was measured in the succeeding secondary reaction, which showed that the optimum final concentration of kaolin lies within the range of 1 to 3 mg/ml, particularly, within the range of 1.25 to 2 mg/ml.

(7) Optimum Reaction Time for the Primary Reaction

The primary reaction was carried out over different periods of time, and the activity of kallikrein thus formed was measured in the succeeding secondary reaction. It was found that a linear relationship between the reaction time and kallikrein activity holds within the reaction time range of 0 to 20 minutes, indicating that the primary reaction time should not exceed 20 minutes.

(8) Amount of LBTI Used in the Primary Reaction

The primary reaction was carried out at 0° C. for 20 minutes, LBTI solutions of different concentrations were added, and 0.1 ml of each reaction mixture was subjected to the secondary reaction to measure the kallikrein activity.

It was demonstrated that LBTI, if added at a final concentration of 4 mg/ml or more, completely inhibits the action of F-XIIa. No significant drop in kallikrein activity was observed with LBTI of up to 15 mg/ml concentration.

(9) Effect of Human Plasma Concentration in the Primary Reaction

The primary reaction was carried using human plasma of different dilutions, and the activity of kallikrein thus formed was measured in the succeeding secondary reaction. A linear relationship was observed between the dilution and kallikrein activity within the dilution range of 1/5 to 1/10.

(10) Substrate Concentration in the Secondary Reaction

The secondary reaction was carried out at 30° C. for 20 minutes using, as synthetic substrate, D-Pro-Phe-Arg-pNA of different concentrations. The $K_m$ value for the secondary reaction was found to be 0.34 mM.

(11) Amount of Enzyme Used in the Secondary Reaction

The secondary reaction was carried out using different amounts of enzyme (namely, different amounts of the primary reaction mixture) to study the relationship between the amount of enzyme and kallikrein activity. A linear relationship was observed with the amount of the primary reaction mixture up to 0.1 ml.

(12) Reaction Time for the Secondary Reaction

The secondary reaction was carried out over different periods of time to study the relationship between the reaction time and kallikrein activity. A linear relationship was observed within the reaction time range of 0 to 20 minutes, indicating that the secondary reaction time should not exceed 20 minutes.

(13) Optimum pH for the Secondary Reaction

The secondary reaction was carried out in 100 mM Tris-HCl buffer solutions of different pH levels to study the relationship between the pH and kallikrein activity. It was demonstrated that the optimum pH for the secondary reaction lies within the range of 7.0 to 9.0, particularly within the range of 7.5 to 8.5.

EXAMPLE 2

Described below is an example which employed human plasma as animal plasma, CHFI as specific inhibitor against F-XIIa, and Z-Phe-Arg-MCA as specific substrate for kallikrein.

(1) Primary Reaction

The same formulation as in EXAMPLE 1 was used in this case too.

The reactant mixture was allowed to stand for 20 minutes in an ice/water bath to effect the primary reaction, which was terminated by addition of 0.5 ml CHFI solution [3 mg/ml in 50 mM Tris-HCl buffer (pH 8.0, 0° C.)] to make the primary reaction mixture. It may also be prepared by taking 0.2 ml of the reaction mixture before termination and adding it to 0.1 ml CHFI solution.

(2) Secondary Reaction

| Primary reaction mixture | 0.1 ml |
| Synthetic substrate | 0.12 ml |
| Buffer solution | 0.18 ml |

In the above formulation, the synthetic substrate was 10 mM solution of Z-Phe-Arg-MCA (a fluorescent substrate) in dimethylsulfoxide, and the buffer solution was 100 mM Tris-HCl buffer (pH 8.0).

The above mixture was allowed to stand at 30° C. for 20 minutes to effect the secondary reaction, 2 ml of 0.1M acetic acid was added, suspended solids, if any, were removed by centrifugation, and the amount of 7-amino-4-methylcoumarin was fluorometrically determined ($E_x$: 380 nm; $E_m$: 460 nm).

(3) Conditions for the primary and secondary reactions were studied in the same way as in EXAMPLE 1.

In the primary reaction, the action of F-XIIa could be inhibited by CHFI solutions of 2 mg/ml and higher concentrations.

The primary reaction in this case differs from that in EXAMPLE 1 only in that a CHFI solution was used to terminate the reaction, all the other conditions being the same as those in EXAMPLE 1.

In the secondary reaction, the optimum pH was in the range of 7.0 to 9.0, particularly in the range of 7.5 to 8.5, and the $K_m$ value for the synthetic fluoroescent substrate, Z-Phe-Arg-MCA, was about 1 mM.

A linear relationship between the secondary reaction time and kallikrein activity was observed within the reaction time range of 0 to 30 minutes, indicating that the secondary reaction time should not exceed 30 minutes.

EXAMPLE 3

Detailed below is an example in which freeze-dried human plasma was used as animal plasma.

(1) Primary Reaction

| Freeze-dried human plasma | 0.1 ml |
| Aqueous suspension of kaolin | 0.5 ml |
| Aqueous solution of sodium chloride<br>Aqueous solution of drug being tested<br>Distilled water | 0.4 ml |

The freeze-dried human plasma was dissolved in distilled water and then diluted with physiological saline to such a concentration that kallikrein activity of 1.6 to 2.2 mU will be exhibited in the secondary reaction.

The kaolin suspension, sodium chloride solution, reaction temperature and time, and termination operation were the same as in EXAMPLE 1.

(2) The secondary reaction was carried out in the same manner as in EXAMPLE 1.

(3) Studies on the conditions for the primary and secondary reactions made in the same manner as in EXAMPLE 1 showed that freeze-dried human plasma can be used under the same conditions as fresh human plasma.

EXAMPLE 4

Described below is an example in which rat plasma was used as animal plasma.

(1) Preparation of Citrate-Containing Rat Plasma

A blood sample, taken from the abdominal aorta of an etherized rat in the presence of sodium citrate (blood: 3.8% sodium citrate=9:1), was centrifuged and the supernatant was collected as citrate-containing rat plasma.

(2) Primary Reaction

| Rat plasma | 0.1 ml |
| Aqueous suspension of kaolin | 0.5 ml |
| Aqueous solution of sodium chloride<br>Aqueous solution of drug being tested<br>Distilled water | 0.4 ml |

In the above formulation, the rat plasma had been diluted with physiological saline by a factor of 3 to 5, and the kaolin suspension and the sodium chloride solution were the same as used in EXAMPLE 1. The above mixture was allowed to stand at 0° C. for 15 minutes to effect the primary reaction, which was terminated by addition of 0.5 ml LBTI solution [45 mg/ml in 50 mM Tris-HCl buffer (pH 8.0)].

(3) Secondary Reaction

The secondary reaction was carried out in much the same manner as in EXAMPLE 1, except that the reaction was continued for 30 minutes.

(4) Conditions for the primary and secondary reactions were studied in the same way as in EXAMPLE 1.

It was found that, in the primary reaction, the optimum pH lies in the range of 7.0 to 9.0, particularly, in the range of 7.5 to 8.5, the optimum concentration of sodium chloride solution is in the range of 0 to 150 mM, particularly, in the range of 25 to 125 mM, and the optimum concentration of kaolin suspension is in the range of 1 to 3.5 mg/ml, particularly in the range of 1.5 to 3 mg/ml.

The primary reaction time should preferably be within 20 minutes, because a linear relationship between the reaction time and kallikrein activity was observed within the reaction time range of 0 to 20 minutes.

For the secondary reaction, it was demostrated that the optimum pH lies in the range of 7 to 9 and the $K_m$ value for D-Pro-Phe-Arg-pNA is 0.29 mM.

A linear relationship between the reaction time and kallikrein activity was observed within the reaction time range of 0 to 60 minutes. Hence, the secondary reaction should not exceed 60 minutes, and should preferably be about 30 minutes in actual practice.

EXAMPLE 5

Described below is an example in which dextran sulfate (M.W.: approximately 500,000) was used as the F-XII activator. The other conditions were the same as in EXAMPLE 1, except that fresh human plasma and freeze-dried human plasma were employed as animal plasma.

(1) The optimum final concentration of dextran sulfate was in the range of 1 to 5 μg/ml, particularly in the range of 1.5 to 3 μg/ml.

(2) The optimum sodium chloride concentration in the primary reaction was in the range of 50 to 85 mM, particularly in the range of 70 to 80 mM.

(3) A linear relationship was observed between the secondary reaction time and kallikrein activity over the reaction time range of 4 to 20 minutes.

(4) The optimum pH for the primary reaction was in the range of 7.8 to 8.3.

As is apparent from the above result, the method of this invention may be successfully practiced by using dextran sulfate as F-XII activator in place of kaolin suspension.

EXAMPLE 6

(Assay of Inhibitory Action Against Bradykinin Liberation)

It was tested whether a test drug inhibits the production of bradykinin—a substance inducing pains and inflammation—in the reaction system of this invention.

o-Phenanthroline, an inhibitor against kininase activity, was added to the primary reaction system in EXAMPLE 1 to suppress the decomposition of bradykinin. At the end of the primary reaction, acetone was added to the primary reaction mixture (final concentration: 50% acetone) to extract bradykinin adsorbed on the kaolin added as F-XII activator.

The amount of bradykinin formed was determined by the radioimmunoassay according to the procedure given below. The acetone extract of bradykinin prepared above (200 μl) was mixed with 200 μl of a buffer solution (Tris-HOAc buffer solution containing 0.1% gelatin, 7 mM calcium chloride, 0.01% Tween-20 and 0.02% sodium azide; pH 8.5), 200 μl of $^{125}$I-Tyr-bradykinin (about 50,000 cpm/ml) and 200 μl of anti-bradykinin rabbit antiserum (1:15,000 dilution), and the mixture was allowed to stand at 4° C. for 48 hours.

Normal ovine serum (200 μl) and a solution of activated charcoal coated with dextran sulfate (500 μl) were then added, and the resulting mixture was allowed to stand at 4° C. for an additional 30 minutes. The reaction mixture thus obtained was centrifuged to remove the supernatant, and the amount of radiation from the residue was measured with a gamma counter. The quantity of bradykinin contained in the sample was determined from a calibration curve prepared by using standard bradykinin solutions.

The activity of various analgesics (indomethacin, ketoprofen, morphine and aminopyrine) to inhibit the formation of kallikrein was measured by using the reaction system of EXAMPLE 1. Each of these drugs was tested in the form of an aqueous solution adjusted to around neutrality.

The result is shown in FIG. 1. It is clear from the figure that remarkable inhibitory action against the formation of kallikrein was observed with indomethacin and ketoprofen, whose analgesic action is partly due to the inhibitory action against the liberation of bradykinin, and that little of such action was observed with morphine and aminopyrine, which are analgesics that mainly act upon the central nervous system.

The inhibitory action of the test drugs against the liberation of bradykinin (the substance which is the final product in the reaction system of this invention and induces pains and inflammations) was examined.

Drugs which exhibit remarkable inhibitory action against the formation of kallikrein also show outstanding inhibitory action against the liberation of bradykinin.

It is thus clear that inhibition of kallikrein formation (FIG. 1) and inhibition of bradykinin liberation correlate well, indicating the high reliability of the method of this invention as a means of assaying physiologically active substances involved in the kallikrein-kinin system.

As is apparent from the foregoing, the method of this invention is useful for assaying those physiologically active substances which affect the formation of kallikrein, for example, those substances having the inhibitory action against the liberation of bradykinin.

The method of this invention employs a series of complex enzyme reactions involving various types of enzymes, which generally require much time and labor for their isolation and purification. This difficulty is eliminated by the use of animal plasma or a freeze-dried product thereof as the enzyme source, providing an outstanding advantage of the method of this invention. In addition, the reaction system involving a series of enzyme reactions contains a lot of active points that undergo the action of said physiologically active substance (the drug being tested), thus allowing multilateral screening tests to be effected simultaneously by a simple operation.

As stated earlier, the kallikrein-kinin system is closely related to various types of enzyme systems and is involved in many control functions in living bodies. Hence the reaction system of this invention is very useful for assaying the substances which control the actions of prostglandin, leukotriene and thromboxane produced from the arachidonate cascade, blood-pressure controlling substances related to the renin-angiotensin system, those which control the blood coagulation and fibrinolysis systems, and those which control the physiological action of bradykinin (for example, anti-inflammatory, analgesic and antiallergic agents).

What is claimed is:

1. A method of assaying inhibitory action of a kallikrein formation inhibitor, the method comprising forming a reaction mixture consisting essentially of (1) animal plasma, (2) an activator for blood coagulation factor XII, (3) an electrolyte and (4) a kallikrein formation inhibitor to be assayed; incubating said reaction mixture; adding an inhibitor having substantially no effect upon the kallikrein activity and being capable of specifically inhibiting activity of activated blood coagulation factor XII to substantially stop production of kallikrein in said reaction mixture, said adding occurring while a substantially linear relationship exists between reaction time and kallikrein formation; and measuring an amount of kallikrein thus formed.

2. A method of assaying a kallikrein formation inhibitor as defined in claim 1, wherein said animal plasma is human plasma.

3. A method of assaying a kallikrein formation inhibitor as defined in claim 2, wherein said animal plasma is selected from the group of plasma consisting of citrate-containing plasma, and a freezed-dried product obtained therefrom.

4. The method recited in claim 1, wherein said amount of kallikrein is measured by adding a buffer solution containing a substrate to kallikrein and measuring reaction product thus formed.

5. A method of assaying a kallikrein formation inhibitor as defined in claim 4, wherein said animal plasma is human plasma.

6. A method of assaying a kallikrein formation inhibitor as defined in claim 4, wherein said animal plasma is plasma of a domestic animal or experimental animal.

7. A method of assaying a kallikrein formation inhibitor as defined in claim 6, wherein said animal plasma is plasma from a mammal selected from the group of mammals consisting of cattle, sheep, pig, horse, goat, monkey, dog, cat, rabbit, guinea pig, rat and mouse.

8. The method recited in claim 1, wherein said reaction proceeds at a temperature of from 0° to 4° C.

9. The method recited in claim 1, wherein said animal plasma is diluted 5-10 times.

10. A method of assaying a kallikrein formation inhibitor as defined in claim 1, wherein said activator for blood coagulation factor XII is an aqueous suspension of kaolin.

11. A method of assaying a kallikrein formation inhibitor as defined in claim 1, wherein said electrolyte is a compound containing a monovalent cation.

12. A method of assaying a kallikrein formation inhibitor as defined in claim 1, wherein said monovalent cation is sodium ion.

13. A method of assaying inhibitory action of a kallikrein formation inhibitor, the method comprising forming a reaction mixture in which pre-kallikrein is converted to kallikrein; incubating said reaction mixture; stopping production of kallikrein in the reaction mixture by adding an inhibitor having substantially no effect upon the kallikrein activity and being capable of specifically inhibiting activity of activated blood coagulation factor XII, said adding occurring while a substantially linear relationship exists between reaction time and kallikrein formation; and measuring an amount of kallikrein thus formed.

* * * * *